US00PP16301P2

(12) United States Plant Patent
Fick

(10) Patent No.: US PP16,301 P2
(45) Date of Patent: Feb. 28, 2006

(54) ***ANISODONTEA* PLANT NAMED 'ELEGANT LADY'**

(50) Latin Name: ***Anisodontea scabrosa*×*Anisodontea elegans***
Varietal Denomination: Elegant Lady

(76) Inventor: Paul Johannes Hendrik Fick, P.O. Box 4183, George East, 6539 (ZA)

( * ) Notice: Subject to any disclaimer, the term of this patent is extended or adjusted under 35 U.S.C. 154(b) by 58 days.

(21) Appl. No.: 11/000,444

(22) Filed: Nov. 30, 2004

(51) Int. Cl.
*A01H 5/00* (2006.01)

(52) U.S. Cl. ..... Plt./226

(58) Field of Classification Search ..... Plt./226
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct *Anisodontea* plant named 'Elegant Lady', characterized by its upright and somewhat outwardly spreading plant habit; vigorous growth habit; tri-lobed leaves; freely flowering habit; and large light purple-colored flowers.

1 Drawing Sheet

Botanical classification/cultivar designation: *Anisodontea scabrosa*×*Anisodontea elegans* cultivar Elegant Lady.

BACKGROUND OF THE INVENTION

The present invention relates to a new and distinct cultivar of *Anisodontea,* botanically known as *Anisodontea scabrosa*×*Anisodontea elegans,* and hereinafter referred to by the name 'Elegant Lady'.

The new *Anisodontea* is a product of a planned breeding program conducted by the Inventor in George, South Africa. The objective of the breeding program is to create new *Anisodontea* cultivars with large and colorful flowers.

The new *Anisodontea* originated from a cross-pollination made by the Inventor in George, South Africa Mexico in September, 1999, of an unnamed selection of *Anisodontea scabrosa,* not patented, as the female, or seed, parent, with an unnamed selection of *Anisodontea elegans,* not patented, as the male, or pollen, parent. The cultivar Elegant Lady was discovered and selected by the Inventor as a flowering plant within the progeny of the stated cross-pollination in a controlled environment in George, South Africa in August, 2000.

Asexual reproduction of the new *Anisodontea* by vegetative cuttings in a controlled environment in George, South Africa since November, 2000, has shown that the unique features of this new *Anisodontea* are stable and reproduced true to type in successive generations.

SUMMARY OF THE INVENTION

The cultivar Elegant Lady has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Elegant Lady'. These characteristics in combination distinguish 'Elegant Lady' as a new and distinct cultivar:

1. Upright and somewhat outwardly spreading plant habit.
2. Vigorous growth habit.
3. Tri-lobed leaves.
4. Freely flowering habit.
5. Large light purple-colored flowers.

Plants of the new *Anisodontea* differ from plants of the female parent selection in the following characteristics:

1. Plants of the new *Anisodontea* have larger and darker green-colored leaves than plants of the female parent selection.
2. Plants of the new *Anisodontea* and the female parent selection differ in leaf shape.
3. Plants of the new *Anisodontea* have larger flowers than plants of the female parent selection.
4. Plants of the new *Anisodontea* and the female parent selection differ in flower coloration.

Plants of the new *Anisodontea* differ from plants of the male parent selection in the following characteristics:

1. Plants of the new *Anisodontea* and the male parent selection differ in leaf shape.
2. Plants of the new *Anisodontea* have darker green-colored leaves than plants of the male parent selection.
3. Plants of the new *Anisodontea* and the male parent selection differ in flower coloration.

Compared to plants of other selections and cultivars of *Anisodontea scabrosa* and *Anisodontea elegans* known to the Inventor, plants of the new *Anisodontea* are more vigorous and have larger leaves and flowers.

BRIEF DESCRIPTION OF THE PHOTOGRAPHS

The accompanying colored photographs illustrate the overall appearance of the new *Anisodontea,* showing the colors as true as it is reasonably possible to obtain in colored reproductions of this type. Colors in the photographs may differ slightly from the color values cited in the detailed botanical description which accurately describe the colors of the new *Anisodontea.*

The photographs at the top of the sheet comprise side perspective view of a typical plant of 'Elegant Lady' grown in a container.

The photographs at the bottom of the sheet are close-up views of typical leaves and flowers of 'Elegant Lady'.

DETAILED BOTANICAL DESCRIPTION

The aforementioned photographs and following observations, measurements and values describe plants grown in an outdoor nursery in Bonsall, Calif. during the spring and summer under conditions which closely approximate commercial production. During the production of the plants, day temperatures ranged from 18 to 35° C. and night temperatures ranged from 10 to 18° C. Plants were about eight weeks old when the photographs and the description were taken. In the description, color references are made to The Royal Horticultural Society Colour Chart, 1995 Edition, except where general terms of ordinary dictionary significance are used.

Botanical classification: *Anisodontea scabrosa*× *Anisodontea elegans* cultivar Elegant Lady.

Parentage:

*Female or seed parent.*—Unnamed selection of *Anisodontea scabrosa,* not patented.

*Male or pollen parent.*—Unnamed selection of *Anisodontea elegans,* not patented.

Propagation:

*Type.*—By vegetative cuttings.

*Time to initiate roots.*—About two weeks.

*Time to develop roots.*—About three to four weeks.

*Root description.*—Fibrous and freely branching.

Plant description:

*Plant form and growth habit.*—Perennial subshrub. Upright and somewhat outwardly spreading plant habit; open plant form; inverted triangle. Vigorous growth habit.

*Branching habit.*—About eight lateral branches per plant; pinching enhances lateral branching.

*Plant height.*—About 78 cm.

*Plant diameter* (*area of spread*).—About 65 cm.

*Lateral branch description.*—Length: About 75 cm. Diameter: About 7 mm. Internode length: About 8 to 10 cm. Texture: Pubescent. Color, younger stems: 146A. Color, older stems: 183A.

*Foliage description.*—Arrangement: Alternate, single. Length: About 4.7 cm. Width: About 5 cm. Shape: Three-lobed with deep sinuses. Apex: Emarginate. Base: Truncate. Margin: Erose; deeply incised; undulate. Texture, upper and lower surfaces: Coarse; pubescent. Venation pattern: Palmate. Color: Developing foliage, upper surface: 146A. Developing foliage, lower surface: 147B. Fully expanded foliage, upper surface: 147A. Fully expanded foliage, lower surface: 147B. Venation, upper and lower surfaces: 147B. Petiole: Length: About 3 cm. Diameter: About 1.5 mm. Texture, upper and lower surfaces: Pubescent. Color, upper and lower surfaces: 146A. Color, lower surface: 183A. Leaf stipules: Quantity: Two per leaf. Length: About 5 mm. Width: About 4 mm. Shape: Elliptical. Color, upper and lower surfaces: 146A to 147A.

Flower description:

*Flower arrangement.*—Flowers arranged at leaf axils. Freely flowering habit, about four to five flower buds, developing and open flowers per node; more than 300 flowers develop per plant. Flowers face upright or outwardly. Flowers not fragrant.

*Flower appearance.*—Large rounded flowers. Flowers persistent.

*Natural flowering season.*—Usually spring and summer or during periods of warm weather.

*Flower longevity.*—Flowers last about seven to ten days on the plant.

*Flower diameter.*—About 4.2 cm.

*Flower length* (*height*).—About 2.5 cm.

*Flower bud.*—Length: About 1 cm. Diameter: About 1.1 cm. Shape: Ovoid. Color: 81B.

*Petals.*—Arrangement: Corolla consists of five petals that are fused at base. Length: About 2.4 cm. Width: About 2.3 cm. Shape: Roughly spatulate. Apex: Cordate. Base: Attenuate. Margin: Entire. Texture, upper and lower surfaces: Smooth, glabrous; satiny. Color: When opening and fully opened, upper surface: 78C; towards the base, 155A; venation, 78A. When opening and fully opened, lower surface: 78C to 78D.

*Sepals.*—Appearance: Five sepals fused into a tubular star-shaped calyx. Length: About 1.3 cm. Width: About 7 mm. Shape: Elliptical. Apex: Acuminate. Margin: Entire. Texture, upper and lower surfaces: Slightly pubescent. Color, upper surface: 146B. Color, lower surface: 146A.

*Bracts.*—Appearance: About three in a single whorl. Length: About 6 mm. Width: About 3 mm. Shape: Linear. Apex: Acute. Margin: Entire. Texture, upper and lower surfaces: Slightly pubescent. Color, upper surface: 146B. Color, lower surface: 146A.

*Peduncles.*—Length: About 2.5 to 4 cm. Diameter: About 1.5 mm. Angle: About 30 to 45° from vertical. Strength: Strong, flexible. Texture: Smooth. Color: 146A.

*Reproductive organs.*—Androecium: Stamen number: About 30 per flower. Filament length: About 1 mm. Anther shape: Oval. Anther length: Less than 1 mm. Anther color: 90B. Amount of pollen: Scarce. Pollen color: 201A. Gynoecium: Quantity: One per flower. Pistil length: About 1.5 cm. Style length: About 1.1 cm. Style color: 62B. Stigma diameter: About 1 mm. Stigma color: 57A. Ovary color: 155A. Seed/fruit: Seed and fruit production has not been observed.

Temperature tolerance: Plants of the new *Anisodontea* have been observed to tolerate temperatures from −4 to 38° C.

Pathogen/pest resistance: Plants of the new *Anisodontea* have not been observed to resistant to pathogens and pests common to *Anisodontea*.

It is claimed:

1. A new and distinct *Anisodontea* plant named 'Elegant Lady', as illustrated and described.

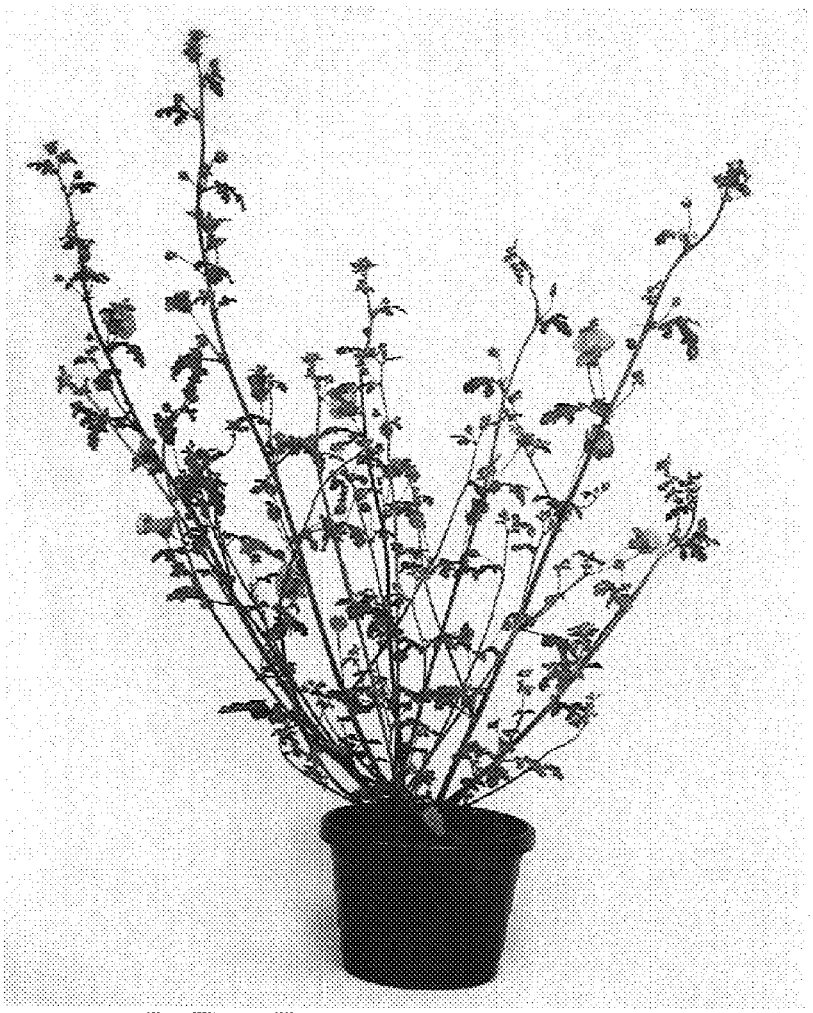
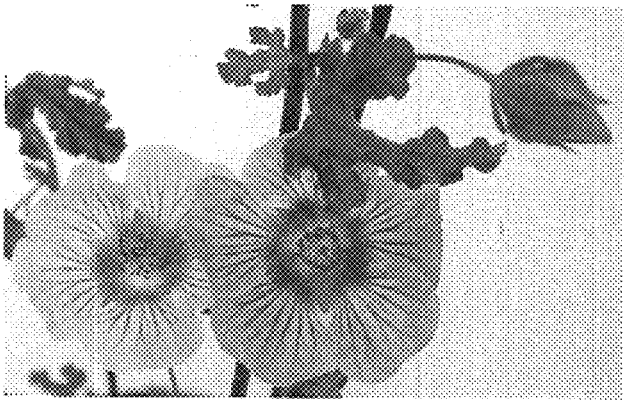
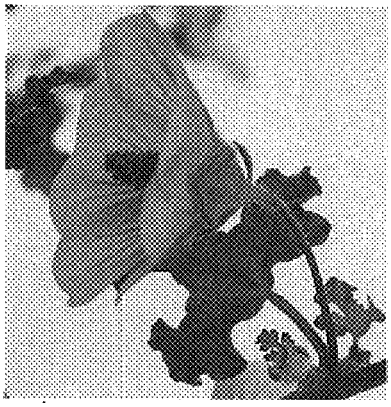

* * * * *